(12) United States Patent
Aono et al.

(10) Patent No.: US 10,281,445 B2
(45) Date of Patent: May 7, 2019

(54) HEADSPACE SAMPLER (75) Inventors: Akira Aono, Kyoto (JP); Yoshitake Yamamoto, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 700 days.

(21) Appl. No.: 14/361,531

(22) PCT Filed: Nov. 30, 2011

(86) PCT No.: PCT/JP2011/077676
§ 371 (c)(1),
(2), (4) Date: Aug. 14, 2014

(87) PCT Pub. No.: WO2013/080333
PCT Pub. Date: Jun. 6, 2013

(65) Prior Publication Data
US 2014/0345365 A1    Nov. 27, 2014

(51) Int. Cl.
*G01N 1/02* (2006.01)
*G01N 33/00* (2006.01)
*G01N 1/22* (2006.01)
*G01M 3/02* (2006.01)
(Continued)

(52) U.S. Cl.
CPC ............ *G01N 33/007* (2013.01); *G01M 3/02* (2013.01); *G01M 3/205* (2013.01);
(Continued)

(58) Field of Classification Search
CPC ............................................ G01N 2001/2229
See application file for complete search history.

(56) References Cited

U.S. PATENT DOCUMENTS 4,518,396 A * 5/1985 Rawson .................... C07C 7/11
48/127.3
4,704,897 A * 11/1987 Kawase .................. G01M 3/22
73/40.5 R
(Continued)

FOREIGN PATENT DOCUMENTS

CA    2 522 253 A1    10/2004
CN    1 806 165 A    7/2006
(Continued)

OTHER PUBLICATIONS

International Preliminary Report on Patentability for PCT/JP2011/077676 dated Jun. 3, 2014.
(Continued)

*Primary Examiner* — Son T Le
*Assistant Examiner* — Alex T Devito
(74) *Attorney, Agent, or Firm* — Sughrue Mion, PLLC (57) ABSTRACT

A headspace sampler includes: a sample gas collection channel whose one end communicates with a needle; a pressure gas introduction channel and an exhaust channel that communicate with the other end of the channel in parallel via a branching pipe; a pressure control device that delivers pressure gas to the pressure gas introduction channel at a predetermined pressure; solenoid valves provided in the pressure gas introduction channel and the exhaust channel, respectively; and switching means for switching a state where a measuring pipe is inserted in the sample gas collection channel and a state where the measuring pipe is shorted away from the channel, wherein a pressure sensor is provided on an upstream side of the solenoid valve in the exhaust channel.

9 Claims, 6 Drawing Sheets (51) Int. Cl.
*G01M 3/20* (2006.01)
*G01M 3/32* (2006.01)
*G01N 30/06* (2006.01)

(52) U.S. Cl.
CPC ........ *G01M 3/3272* (2013.01); *G01N 1/2226* (2013.01); *G01N 30/06* (2013.01); *G01N 2001/2229* (2013.01)

(56) References Cited

U.S. PATENT DOCUMENTS

| | | | |
|---|---|---|---|
| 6,016,792 A * | 1/2000 | Kawano | F02M 25/0809 123/198 D |
| 2002/0066712 A1 | 6/2002 | Brockwell | |
| 2006/0099716 A1 | 5/2006 | Tipler et al. | |
| 2006/0099718 A1 | 5/2006 | Tipler et al. | |
| 2010/0107730 A1 | 5/2010 | Aono | |

FOREIGN PATENT DOCUMENTS

| | | |
|---|---|---|
| CN | 1 806 170 A | 7/2006 |
| EP | 1 613 943 A1 | 1/2006 |
| EP | 1 850 128 A1 | 10/2007 |
| EP | 1 682 885 A1 | 7/2010 |
| JP | 9-184793 A | 7/1997 |
| JP | 10-185776 A | 7/1998 |
| JP | 11-258244 A | 9/1999 |
| JP | 2000-283880 A | 10/2000 |
| JP | 2002-005913 A | 1/2002 |
| JP | 2003-75230 A | 3/2003 |
| JP | 2003-075230 A | 3/2003 |
| JP | 2006-523825 A | 10/2006 |
| JP | 2006-524796 A | 11/2006 |
| JP | 2010-112761 A | 5/2010 |
| JP | 3159793 U | 6/2010 |
| WO | 2004/092711 A1 | 10/2004 |

OTHER PUBLICATIONS

International Search Report of PCT/JP2011/077676, dated Jan. 17, 2012.
Chinese Office Action dated Jun. 30, 2015 in Chinese Patent Application No. 201180076305.5.

* cited by examiner

HEADSPACE SAMPLER

CROSS REFERENCE TO RELATED APPLICATIONS

This application is a National Stage of International Application No. PCT/JP2011/077676 filed Nov. 30, 2011, the contents of all of which are incorporated herein by reference in their entirety.

TECHNICAL FIELD

The present invention relates to a headspace sampler that collects a sample gas volatilized from a liquid sample or from a solid sample by the headspace method and introduces the sample gas into a gas analyzer, such as a gas chromatograph or a gas chromatograph mass spectrometer.

BACKGROUND ART

A headspace sampler heats a liquid sample or a solid sample stored in a container at a preset temperature for a preset period of time to vaporize components having relatively low boiling points, collects a predetermined amount of gas containing these components (sample gas) from the upper space (headspace) of the container, and introduces the sample gas into a gas analyzer, such as a gas chromatograph (for example, refer to Patent Literature 1). Such a headspace sampler is suitably used for, e.g., chromatograph analysis of flavor ingredients in food, volatile organic compounds in water or the like.

Figure 8:
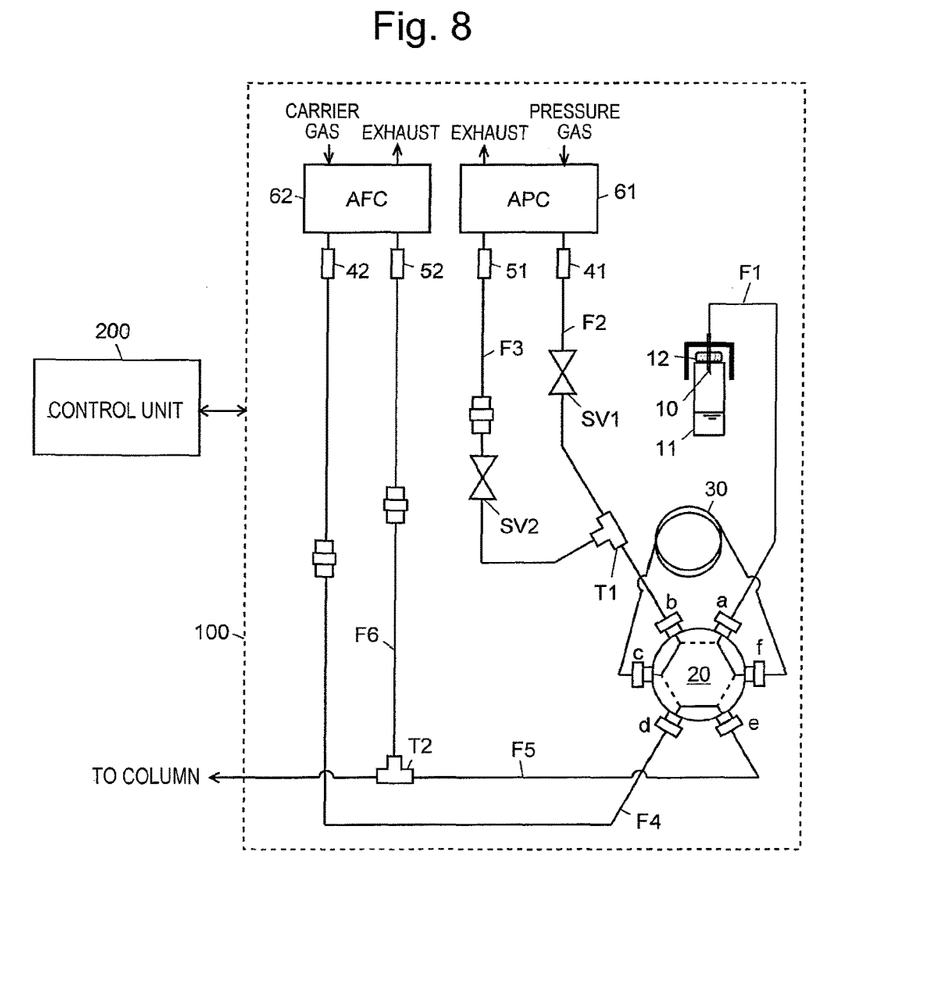
FIG. 8 is a diagram showing a schematic configuration of a conventional headspace sampler.

FIG. 8 shows an example of a configuration of a conventional headspace sampler. This device includes a sampling unit 100 and a control unit 200, and collects a predetermined amount of sample gas from a sample container 11 set in the sampling unit 100 and introduces into a column (not shown) provided at a chromatograph analyzer.

In the sampling unit 100, a channel switching valve 20 is a rotary 6-port 2-position valve that includes six ports, or ports a to f, and switches to a connection state indicated by solid lines in FIG. 8 (hereinafter, referred to as a "load state") or a connection state indicated by broken lines (hereinafter, referred to as an "injection state") under control by the control unit 200.

The port a of the channel switching valve 20 communicates with a needle 10 for collecting sample gas (hereinafter, a channel connecting the port a to the needle 10 is referred to as a "channel F1"). The port b communicates with a gas inlet 41 for introducing gas (pressure gas) for pressurizing the inside of the sample container 11 and a gas outlet 51 for discharging the sample gas, via a branching pipe T1 (hereinafter, a channel between the branching pipe T1 and the gas inlet 41 is referred to as a "channel F2", and a channel between the branching pipe T1 and the gas outlet 51 is referred to as a "channel F3"). On the channel F2, a solenoid valve SV1 is provided. On the channel F3, a solenoid valve SV2 is provided. The port c communicates with the port f via a measuring pipe 30 having a prescribed volume. The port d communicates with a gas inlet 42 for introducing carrier gas (hereinafter, a channel connecting the port d to the gas inlet 42 is referred to as a "channel F4"). The port e communicates with an inlet end of a column and a split channel F6, via a branching pipe T2 (hereinafter, a channel from the port e to the column is referred to as a "channel F5"). The split channel F6 is for discharging a part of sample gas without delivery to the column. At the tip end of this channel, a gas outlet 52 for discharging the sample gas is provided.

The gas inlet 41 and the gas outlet 51 communicate with a pressure control device ("APC" in the diagram) 61. Through this pressure control device 61, the pressure of gas flowing through the gas inlet 41 and the gas outlet 51 is controlled. On the other hand, the gas inlet 42 and the gas outlet 52 are controlled by a flow rate control device (AFC) 62. By means of this flow rate control device 62, the flow rate of gas flowing through the gas inlet 42 and the gas outlet 52 is controlled.

Hereinafter, procedures during introduction of sample gas into the column by the sampling unit 100 are described.

(i) Pressurizing Process

First, the solenoid valves SV1 and SV2 are closed, and the channel switching valve 20 is set to be in the load state, and, in this state, the needle 10 penetrates the sample container 11 and the distal end is disposed in the upper space (headspace) of the sample container 11. The sample container 11 is then heated by heating means, not shown, to a predetermined temperature. Subsequently, the solenoid valve SV1 is opened to introduce pressure gas from the gas inlet 41. Thus, the pressure gas is introduced into the sample container 11 and the inside of the sample container 11 is pressurized.

(ii) Equilibration Process

Next, the solenoid valve SV1 is closed, and this standby state is maintained for a predetermined time (which is referred to as "waiting time"). Thus, over a path from the sample container 11 then through the channel F1→the port a→the port f→the measuring pipe 30→the port c→the port b to the branching pipe T1, a region of the channel F2 between the branching pipe T1 and the solenoid valve SV1, and a region of the channel F3 between the branching pipe T1 and the solenoid valve SV2, the pressure and temperature of the inner space are equilibrated.

(iii) Sample Gas Collection Process

Subsequently, when the solenoid valve SV2 is opened, gas (sample gas) containing sample components vaporized in the sample container 11 flows through the needle 10 into the channel F1, passes through the channel switching valve 20 and flows into the measuring pipe 30. At this time, a part of the gas flowing into the measuring pipe 30 passes through the channel switching valve 20, the branching pipe T1 and the channel F3 and is discharged from the gas outlet 51. During the foregoing process, the carrier gas passes in an order from the gas inlet 42 to the channel F4→the port d→the port e→the channel F5 and flows into the column.

(iv) Sample Gas Introduction Process

Next, after the channel switching valve 20 is switched to the injection state, the carrier gas supplied from the gas inlet 42 passes in an order of the channel F4→the port d→the port c→the measuring pipe 30→the port f→the port e→the channel F5 and flows into the column. Thus, the predetermined amount of sample gas held in the measuring pipe 30 is introduced into the column together with the flow of the carrier gas. Parts of the carrier gas and sample gas flowing from the port e of the channel switching valve 20 and reaching the branching pipe T2 flow into the split channel F6 at a predetermined split ratio and are discharged from the gas outlet 52.

CITATION LIST

Patent Literature

[Patent Literature 1] JP 2002-005913 A

SUMMARY OF INVENTION

Technical Problem

Typically, the sample container 11 used in the headspace sampler as described above has a structure including a vial made of glass tightly closed with a cover (septum) 12 made of silicone rubber. The sample gas is collected by piercing the cover with the needle 10. Accordingly, if the gas-tightness of the sample container 11 is insufficient owing to improper closure or the like, gas sometimes leaks from the sample container 11. If such a leak of gas occurs at any point during the pressurizing process to the sample gas collection process, the sample gas is diluted or the collected amount of sample gas is reduced. Accordingly, there is a possibility that analysis cannot be accurately performed. However, the conventional headspace sampler cannot detect a leak of gas from such a sample container.

Furthermore, also in the case where the inside of the needle 10 in the headspace sampler is clogged, sample gas cannot be appropriately collected, which causes a possibility that a correct analysis result cannot be obtained. However, the conventional headspace sampler cannot detect such clogging of the needle.

The present invention has been developed to solve the aforementioned problems, and has a first object to provide a headspace sampler that can detect occurrence of a leak of gas from the sample container. The present invention also has a second object to provide a headspace sampler that can detect clogging of a needle.

Solution to Problem

A first aspect of a headspace sampler according to the present invention developed to solve the problems, includes:

a) a sample gas collection channel whose one end communicates with a needle;

b) a pressure gas introduction channel and an exhaust channel that communicate with the other end of the sample gas collection channel in parallel via a branching pipe;

c) a first on-off valve provided in the pressure gas introduction channel;

d) a second on-off valve provided in the exhaust channel;

e) a pressure sensor provided at one of positions comprised of a position on the sample gas collection channel, a position on the pressure gas introduction channel and a position between the branching pipe and the second on-off valve of the exhaust channel, and for measuring a pressure in the channel at the position; and f) gas leak determination means for penetrating a sample container with the needle, and subsequently introducing the pressure gas into the pressure gas introduction channel by closing the second on-off valve and opening the first on-off valve, and for determining a leak of gas from the sample container based on a measured value of the pressure sensor.

In the headspace sampler having the above-described configuration, if a leak of gas from the sample container occurs, the measured value of the pressure sensor in the case where the needle penetrates the sample container, the second on-off valve is closed and the pressure gas is introduced into the pressure gas introduction channel is smaller than that in a normal state (i.e., in the case where there is no leak). Therefore, according to the gas leak determination means, a leak of gas from the sample container can be determined based on the measured value of the pressure sensor in the above-described pressurizing process.

A second aspect of a headspace sampler according to the present invention developed to solve the problems, includes:

a) a sample gas collection channel whose one end communicates with a needle;

b) a pressure gas introduction channel and an exhaust channel that communicate with the other end of the sample gas collection channel in parallel via a branching pipe;

c) a first on-off valve provided in the pressure gas introduction channel;

d) a second on-off valve provided in the exhaust channel;

e) a pressure sensor provided at one of positions comprised of a position on the sample gas collection channel, a position between the branching pipe and the first on-off valve of the pressure gas introduction channel, and a position between the branching pipe and the second on-off valve of the exhaust channel, and for measuring a pressure in the channel at the position; and f) gas leak determination means for introducing a pressure gas from the pressure gas introduction channel into the sample container, for subsequently creating a state where both the first on-off valve and the second on-off valve are closed, for maintaining the state for a predetermined waiting time period, and for determining a leak of gas from the sample container based on a measured result of the pressure sensor during the waiting time period.

If no leak of gas occurs from the sample container, the measured value of the pressure sensor during the waiting time is hardly changed. However, if a leak of gas from the sample container occurs, the measured value of the pressure sensor gradually decreases during the waiting time. Accordingly, the configuration as described above can detect a smaller level leak of gas.

A third aspect of a headspace sampler according to the present invention developed to solve the problems, includes:

a) a sample gas collection channel whose one end communicates with a needle;

b) a pressure gas introduction channel and an exhaust channel that communicate with the other end of the sample gas collection channel in parallel via a branching pipe;

c) a first on-off valve provided in the pressure gas introduction channel;

d) a second on-off valve provided in the exhaust channel;

e) a pressure sensor provided at one of positions comprised of a position on the sample gas collection channel, a position on the pressure gas introduction channel, and a position between the branching pipe and the second on-off valve of the exhaust channel, and for measuring a pressure in the channel at the position; and f) clogging determination means for delivering the pressure gas into the pressure gas introduction channel by closing the second on-off valve and opening the first on-off valve, and for determining clogging of the needle based on a measured result of the pressure sensor.

In the headspace sampler having the foregoing configuration, if the inside of the needle is clogged, the measured value of the pressure sensor in the case where the first on-off valve is opened with the second on-off valve being closed and the pressure gas is introduced into the pressure gas introduction channel is higher than that in a normal state (i.e., in case where there is no clogging). Accordingly, the clogging determination means can determine whether the needle is clogged or not based on the measured value of the pressure sensor at this time.

The pressure sensor in the headspace samplers according to the first and third aspects of the present invention may use a pressure sensor included in a pressure control device conventionally provided at an inlet of the pressure gas introduction channel. Alternatively, this sensor may be separately provided.

It should be noted that if a pressure sensor internally including a component made of resin is arranged on the pressure gas introduction channel or the sample gas collection channel, there is a possibility that gas occurring from the resin is mixed into the pressure gas in a process where the pressure gas is introduced into the sample container via these channels. In order to prevent this mixture, it is preferred to adopt a sensor without a component made of resin as the pressure sensor or to arrange the pressure sensor between the branching pipe and the second on-off valve of the exhaust channel.

It is preferred that the headspace sampler according to the present invention further be provided with notification means for notifying a user of a determination result by the gas leak determination means or the clogging determination means.

It is preferred that the headspace sampler according to the present invention have the configuration further including storing means for recording a determination result by the gas leak determination means or clogging determination means and/or a measured value of the pressure sensor constituting grounds for the determination.

Advantageous Effects of Invention

As described above, by the headspace sampler according to the first aspect or the second aspect of the present invention, it can be easily detected whether a leak of gas occurs at the sample container or not. Furthermore, by the headspace sampler introduction device according to the third aspect of the present invention, it can be easily detected whether the needle is clogged or not.

DESCRIPTION OF EMBODIMENTS

Hereinafter, modes for implementing the present invention are described, exemplifying embodiments.

First Embodiment

Figure 1:
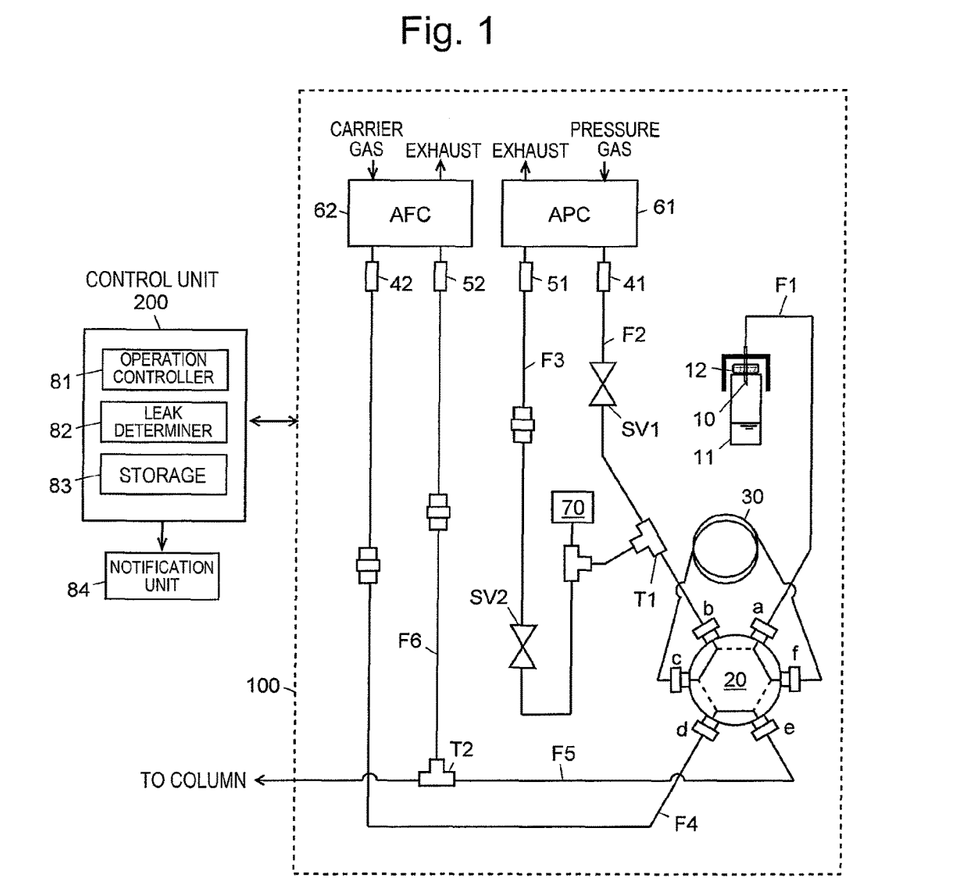
FIG. 1 is a diagram showing a schematic configuration of a headspace sampler according to a first embodiment of the present invention.

FIG. 1 is a diagram showing a schematic configuration of a headspace sampler according to an embodiment of the present invention. It should be noted that, according to this diagram, the sampling unit 100 adopts a split method. It is, however, a matter of course that this unit may adopt a splitless method. Furthermore, the same numerals are assigned to the same structural elements as those in FIG. 8 having already been described. The detailed description is omitted unless specifically required.

The headspace sampler according to this embodiment includes a function of determining a leak of gas in a sample container 11. The fundamental configuration is the same as that of FIG. 8 having already been described. However, as a characteristic structural element, this device includes a pressure sensor 70 that is for measuring the gas pressure in a channel over a region between the branching pipe T1 and the solenoid valve SV2 on the channel F3 and is thus provided in this region. Furthermore, a control unit 200 is provided with a leak determiner 82, and connected with a notification unit 84.

The control unit 200 includes, in addition to the leak determiner 82, an operation controller 81 and a storage 83. The operation controller 81 controls the operations of solenoid valves SV1 and SV2, a channel switching valve 20, a pressure control device (APC) 61, a flow rate control device (AFC) 62, the pressure sensor 70 and the like of the sampling unit 100. The leak determiner 82 determines a leak of gas in the sample container 11 based on a measured result of the pressure sensor 70. The storage 83 includes a storing device, such as a hard disk device, and stores a determination result and the like by the leak determiner 82.

The pressure control device 61 internally includes a connection channel that connects a pressure gas source (not shown) including a gas cylinder and the like to a gas inlet 41, a pressure gage provided in the connection channel, and an on-off valve for opening and closing the channel (all the elements are not shown). This device has a configuration of performing control to open the on-off valve if the measured value of the pressure gage is lower than a preset target value $P_1$, and close the on-off valve if the measured value of the pressure gage is higher than the target value $P_1$.

The control unit 200 may be, for example, a general-purpose personal computer, and can achieve various controls and data processing functions by executing dedicated control/processing software installed in the computer. It should be noted that the control unit 200 may be dedicated hardware.

The notification unit 84 is for notifying a user of a determination result by the leak determiner 82. For example, this unit may include a display device, such as a monitor, and display the determination result on the monitor. The notification unit 84 may include audio output means, such as a speaker, and issue notification of the determination result by means of audio in addition to or instead of notification through the display device.

In the sample introduction channel 100, the channel F1 and a region from the port a of the channel switching valve 20 to the branching pipe T1 correspond to a sample gas introduction channel in the present invention. Furthermore, the channel F2 and the connection channel correspond to a pressure gas introduction channel, and the channel F3 corresponds to an exhaust channel. Moreover, the solenoid valves SV1 and SV2 correspond to a first on-off valve and a second on-off valve, respectively.

Figure 2:
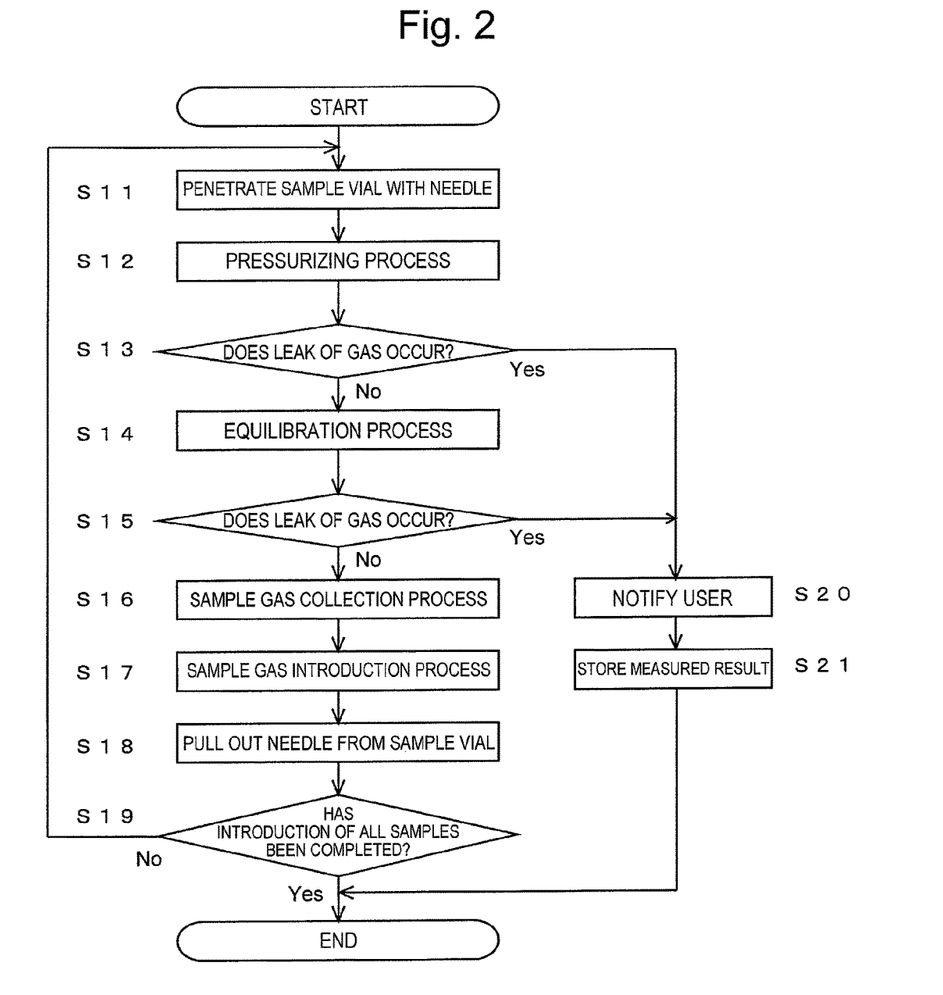
FIG. 2 is a flowchart showing operation of the headspace sampler according to this embodiment.

Subsequently, operations of the headspace sample analyzer according to this embodiment during sample gas introduction into a gas analyzer are described with reference to a flowchart of FIG. 2.

First, the solenoid valves SV1 and SV2 are closed, the channel switching valve 20 is set to be in the load state and then, in this state, a cover 12 of one sample container 11 among multiple sample containers (not shown) set in the sampling unit 100 is pierced with a needle 10, and the distal end of the needle 10 is disposed in the upper space in the sample container 11 (step S11). Subsequently, the sample container 11 is heated by heating means, not shown, to a predetermined temperature to vaporize a sample in the sample container 11. Subsequently, the solenoid valve SV1 is opened to introduce pressure gas from a pressure gas source through the pressure control device 61 into the gas inlet 41. Thus, the pressure gas introduced from the gas inlet 41 passes through the solenoid valve SV1→the branching pipe T1→the port b→the port c→the measuring pipe 30→the port f→the port a→the needle 10 and is introduced into the sample container 11 (step S12).

Figure 3:
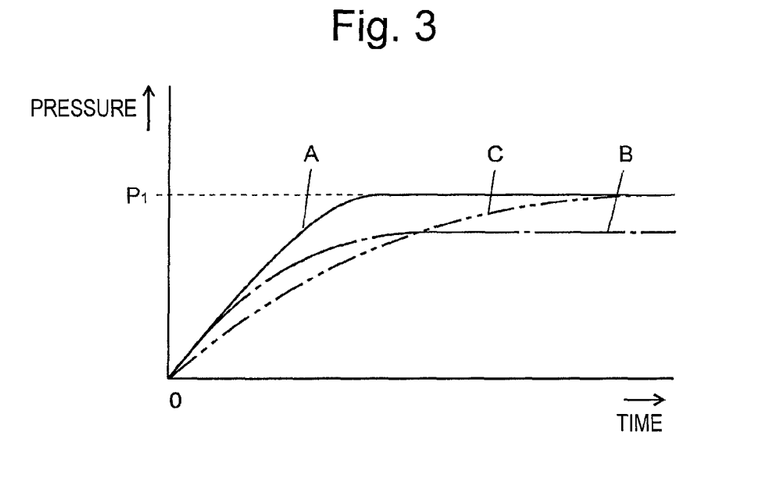
FIG. 3 is a diagram showing an example of a pressure curve in this embodiment.

In this case, after the moment of opening the solenoid valve SV1 (i e , immediately after the start of the pressurizing process), the measured value of the pressure sensor 70 is monitored by the leak determiner 82, and a pressure curve as shown in FIG. 3 is created. On the other hand, the storage 83 preliminarily stores an ideal pressure curve (i.e., in the case of assumption where there is no leak of gas from the sample container 11) preliminarily calculated based on the piping configuration of the sampling unit 100 and delivery conditions of the pressure gas. At the point in time of completion of the pressurizing process (or the point in time when a predetermined time has elapsed after the start of pressurizing), the leak determiner 82 compares a pressure curve created based on the measured values of the pressure sensor 70 with the ideal pressure curve, and determines whether gas leaks from the sample container 11 or not based on whether the degree of coincidence between both the curves is equal to or higher than a predetermined threshold or not (step S13).

In the foregoing step S12, immediately after the solenoid valve SV1 is opened, the measured value of the pressure gage provided in the pressure control device 61 is lower than the target value $P_1$. Accordingly, the on-off valve in the pressure control device 61 is opened, and the pressure gas flows into the channel F2. Subsequently, the measured value of the pressure gage gradually becomes higher. At the time when the measured value exceeds the target value $P_1$, the on-off valve is closed and the supply of the pressure gas to the channel F2 is stopped.

Accordingly, if no gas leaks from the sample container 11, the measured value of the pressure sensor 70 in the pressurizing process sharply rises immediately after the start of the pressurizing process as indicated by a line A in FIG. 3, and levels off after reaching the target value $P_1$. On the contrary, if a gas leaks from the sample container 11, the pressure gas supplied into the channel F2 flows to the outside of the sample container 11. Accordingly, the measured value of the pressure sensor 70 levels off at a value lower than the target value $P_1$ as indicated by a line B in FIG. 3, or reaches the target value $P_1$ as indicated by a line C in FIG. 3 but the time period from the start of the pressurizing process to reaching to the target value is long.

Thus, if the pressure curve created based on the measured value of the pressure sensor 70 substantially matches with the ideal pressure curve (line A in FIG. 3), the leak determiner 82 of this embodiment determines that no leak of gas occurs from the sample container 11. If the curve is largely different from the ideal pressure curve A as indicated by the line B or the line C in FIG. 3, the leak determiner 82 determines that a leak of gas from the sample container 11. It should be noted that, instead of creation of the pressure curve as described above, whether a leak of gas from the sample container 11 occurs or not may be determined by comparing the measured value by the pressure sensor 70 at a predetermined point in time after the start of the pressurization with a value preliminarily calculated as an ideal pressure value at this point in time.

If it is determined that a leak of gas occurs from the sample container 11 in the foregoing step S13, the notification unit 84 notifies the user of this occurrence (step S20), the measured values of the pressure sensor 70 obtained during a period immediately after the start of the pressurizing process to the completion of the determination and/or the determination result in step S13 are stored into the storage 83 (step S21), the solenoid valve SV1 is closed, and the operation of the sampling unit 100 is stopped. It should be noted that recording of the measured value or the determination result into the storage 83 may be performed irrespective of the determination result in the leak determiner 82.

If it is determined that no leak of gas from the sample container 11 in step S13, the solenoid valve SV1 is closed and the state is maintained for a predetermined time (step S14).

Figure 4:
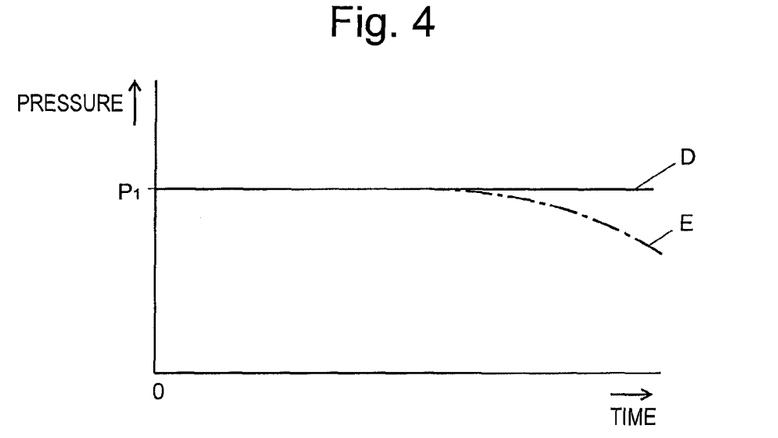
FIG. 4 is a diagram showing another example of a pressure curve in this embodiment.

In this case, after the moment of closing the solenoid valve SV1 (i.e., immediately after the start of the equilibration process), the measured value of the pressure sensor 70 is monitored by the leak determiner 82, and a pressure curve as shown in FIG. 4 is created. On the other hand, the storage 83 preliminarily stores an ideal pressure curve (i.e., in the case of assumption where no gas leaks from the sample container 11) preliminarily calculated based on the piping configuration of the sampling unit 100 and delivery conditions of the pressure gas. At the point in time of completion of the equilibration process (or the point in time when a predetermined time has elapsed after the start of the equilibration process), the leak determiner 82 compares a pressure curve created based on the measured values of the pressure sensor 70 with the ideal pressure curve, and determines whether gas leaks from the sample container 11 or not based on whether the degree of coincidence between both the curves is equal to or higher than a predetermined threshold or not (step S15). Thus, if the pressure curve created based on the measured values of the pressure sensor 70 substantially matches with the ideal pressure curve (for example, line D in FIG. 4), it is determined that no leak of gas occurs from the sample container 11. If the curve is largely different from the ideal pressure curve D as indicated by a line E in FIG. 4, it is determined that gas leaks from the sample container 11. It should be noted that, also in this case, instead of creation of the pressure curve as described above, where there is a leak of gas from the sample container 11 may be determined by comparing the measured value of the pressure sensor 70 at a predetermined point in time after the start of the equilibration process with a value preliminarily calculated as an ideal pressure value at this point in time.

If it is determined that a leak of gas occurs from the sample container 11 in the foregoing step S15, the notification unit 84 notifies the user of this occurrence (step S20), the measured value of the pressure sensor 70 obtained during a period immediately after the start of the equilibration process to the completion of the determination and/or the determination result in step S15 are stored into the storage 83 (step S21), and the sample introduction is stopped. It should be noted that recording of the measured value or the determination result into the storage 83 may be performed irrespective of the determination result in the leak determiner 82.

If it is determined that no leak of gas from the sample container 11 in step S15, the solenoid valve SV2 is subsequently opened. Then, the sample gas containing gas components occurring from the sample in the sample container 11 flows through the needle 10 into the channel F1, passes through the channel switching valve 20 and flows into the measuring pipe 30. Thus, the sample gas is collected into the measuring pipe 30 (step S16). It should be noted that, a part of the gas flowing into the measuring pipe 30 at this time passes through the channel switching valve 20, the branching pipe T1 and the channel F3 and is discharged from the gas outlet 51. On the other hand, during the foregoing process, the carrier gas passes in an order from the gas inlet 42 to the channel F4→the port d→the port e→the channel F5 and flows into the column.

Next, after the channel switching valve 20 is switched to the injection state, the carrier gas supplied from the gas inlet 42 passes in an order of the channel F4→the port d→the port c→the measuring pipe 30→the port f→the port e→the branching pipe T2 and flows into the column. Thus, the predetermined amount of sample gas held in the measuring pipe 30 is introduced into the column together with the flow of the carrier gas (step S17). Parts of the carrier gas and sample gas flowing from the port e of the channel switching valve 20 and reaching the branching pipe T2 flow into the split channel F6 at a predetermined split ratio and are discharged from the gas outlet 52.

After the introduction of the sample gas into the column is completed, the channel switching valve 20 is switched to the load state, and, in the state where the solenoid valves SV1 and SV2 are closed, the needle 10 is pulled out from the sample container 11 (step S18). It is then determined whether introduction of sample gas into the column has been completed for all the sample containers set in the sampling unit 100 or not (step S19). If the introduction for all the samples has been completed, the operation of the sampling unit 100 is finished. If any sample having not been introduced remains, the processing returns to step S11, and the operations of steps S11 to S19 are repeatedly executed until the introduction is completed for all the samples.

As described above, by the headspace sampler according to this embodiment, the pressure sensor is provided on an upstream side of the solenoid valve SV2 in the channel F3, which allows the pressure in the sample container 11 to be measured during the pressurizing process and the equilibration process. Accordingly, whether gas leaks from the sample container 11 or not can be detected.

It should be noted that, the above example adopts the configuration of determining a leak of gas in each of the pressurizing process and the equilibration process. Alternatively, a leak of gas may be determined in any one of both the processes. It should be noted that, in the case of determining in the equilibration process, even a small level leak of gas can be detected. However, in order to achieve a correct determination, the measured value of the pressure sensor 70 is required to be monitored for a relatively long time period. Thus, in the case where only a relatively large leak of gas is required to be detected, it is preferred to detect a leak of gas only in the pressurizing process.

Furthermore, the above example adopts the configuration of notifying the user of occurrence of a leak of gas and subsequently stopping the operation of the sampling unit 100 automatically. Alternatively, the user may be allowed to select whether to stop or continue the operation of the sampling unit 100 when the notification is issued. Alternatively, the user may preliminarily set whether the operation of the sampling unit 100 is stopped or continued when it is determined that a leak of gas occurs, and the determination may be stored in the storage 83, and then the operation of the sampling unit 100 may be controlled according to the setting. It should be noted that even if the user selects the continuation of the operation of the sampling unit 100, the measured value of the pressure sensor 70 and/or the determination results of the leak determiner 82 are recorded in the storage 83. Accordingly, the record may be referred to after the process, and only a sample on which a leak of gas has occurred may be analyzed again. If the analysis result by the gas analyzer is inappropriate, the cause can be identified by referring to the record after the process.

Furthermore, in the above embodiment, the pressure sensor 70 is provided between the branching pipe T1 and the solenoid valve SV2. Alternatively, also in the case of providing the pressure sensor 70 at one of positions comprised of a position between the solenoid valve SV1 and the branching pipe T1, a position between the branching pipe T1 and the port b of the channel switching valve 20, and a position on the channel F1, the same effect as described above can be achieved. In the case of determining a leak of gas only during pressurization, the pressure sensor 70 may be provided between the pressure control device 61 and the solenoid valve SV1. A configuration may be adopted where a leak of gas may be determined in a pressurizing process as described above based on the measured value of the pressure gage provided in the pressure control device 61 (in this case, the pressure gage corresponds to the pressure sensor in the present invention).

Second Embodiment

Figure 5:
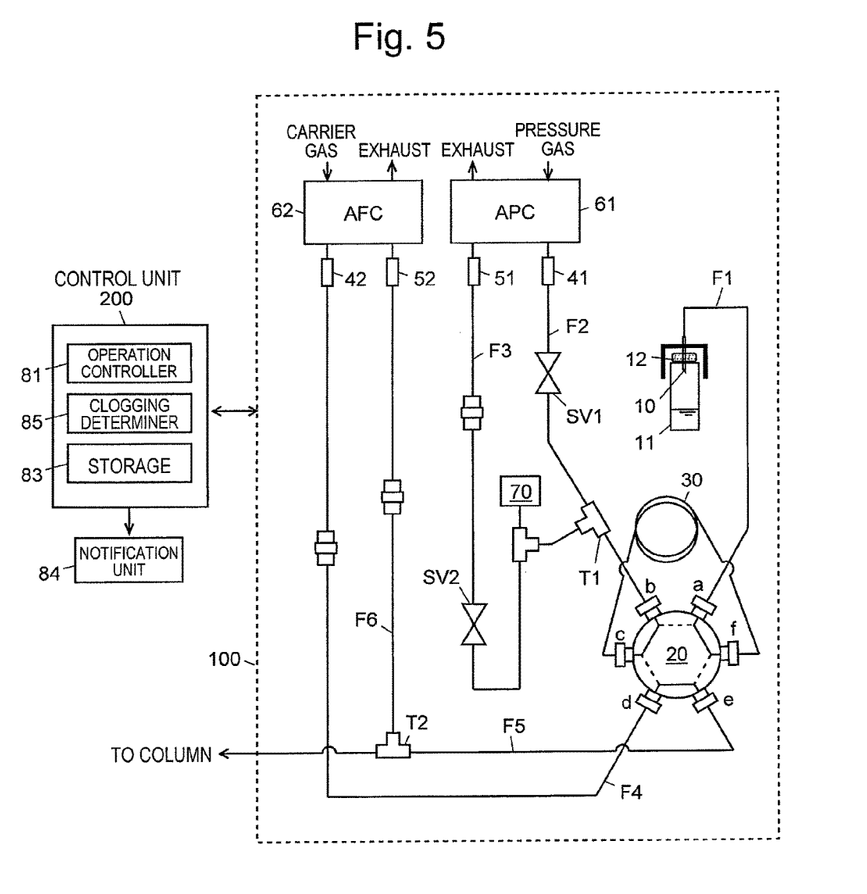
FIG. 5 is a diagram showing a schematic configuration of a headspace sampler according to a second embodiment of the present invention.

Subsequently, another embodiment of a headspace sampler of the present invention is described. FIG. 5 is a diagram showing a schematic configuration of a headspace sampler according to this embodiment. It should be noted that, according to this diagram, the sampling unit 100 adopts a split method. It is, however, a matter of course that this unit may adopt a splitless method. Furthermore, the same numerals are assigned to the same structural elements as those in FIG. 8 having already been described. The detailed description is omitted unless specifically required.

The headspace sampler according to this present embodiment includes a function of determining clogging in a needle 10. The fundamental configuration is the same as that of FIG. 8 having already been described. However, as a characteristic structural element, this device includes a pressure sensor 70 that is for measuring the gas pressure in a channel in a region between the branching pipe T1 and the solenoid valve SV2 on the channel F3 and is thus provided in this region. Furthermore, a control unit 200 is provided with a clogging determiner 85, and connected with a notification unit 84.

The control unit 200 includes, in addition to the clogging determiner 85, an operation controller 81 and a storage 83. The operation controller 81 controls the operations of solenoid valves SV1 and SV2, a channel switching valve 20, a pressure control device (APC) 61, a flow rate control device (AFC) 62, the pressure sensor 70 and the like of the sampling unit 100. The clogging determiner 85 determines clogging of the needle 10 based on the measured result of the pressure sensor 70. The storage 83 includes a storing device, such as a hard disk device, and stores a determination result and the like by the clogging determiner 85.

The pressure control device 61 internally includes a connection channel that connects a pressure gas source (not shown) including a gas cylinder and the like to the gas inlet 41, a pressure gage provided at the connection channel, and an on-off valve for opening and closing the channel (all the elements are not shown). This device has a configuration of performing control to open the on-off valve if the measured value of the pressure gage is lower than a preset target value $P_1$, and close the on-off valve if the measured value of the pressure gage is higher than the target value $P_1$.

The control unit 200 may be, for example, a general-purpose personal computer, and can achieve various controls and data processing functions by executing dedicated control processing software installed in the computer. It should be noted that the control unit 200 may be dedicated hardware.

The notification unit 84 is for notifying a user of a determination result by the clogging determiner 85. For example, this unit may include a display device, such as a monitor, and display the determination result on the monitor. The notification unit 84 may include audio output means, such as a speaker, and issue notification of the determination result by means of audio in addition to or instead of notification through the display device.

In the sample introduction channel 100, the channel F1 and a region from the port a of the channel switching valve 20 to the branching pipe T1 correspond to a sample gas introduction channel in the present invention. Furthermore, the channel F2 and the connection channel correspond to a pressure gas introduction channel, and the channel F3 corresponds to an exhaust channel. Moreover, the solenoid valves SV1 and SV2 correspond to a first on-off valve and a second on-off valve, respectively.

Figure 6:
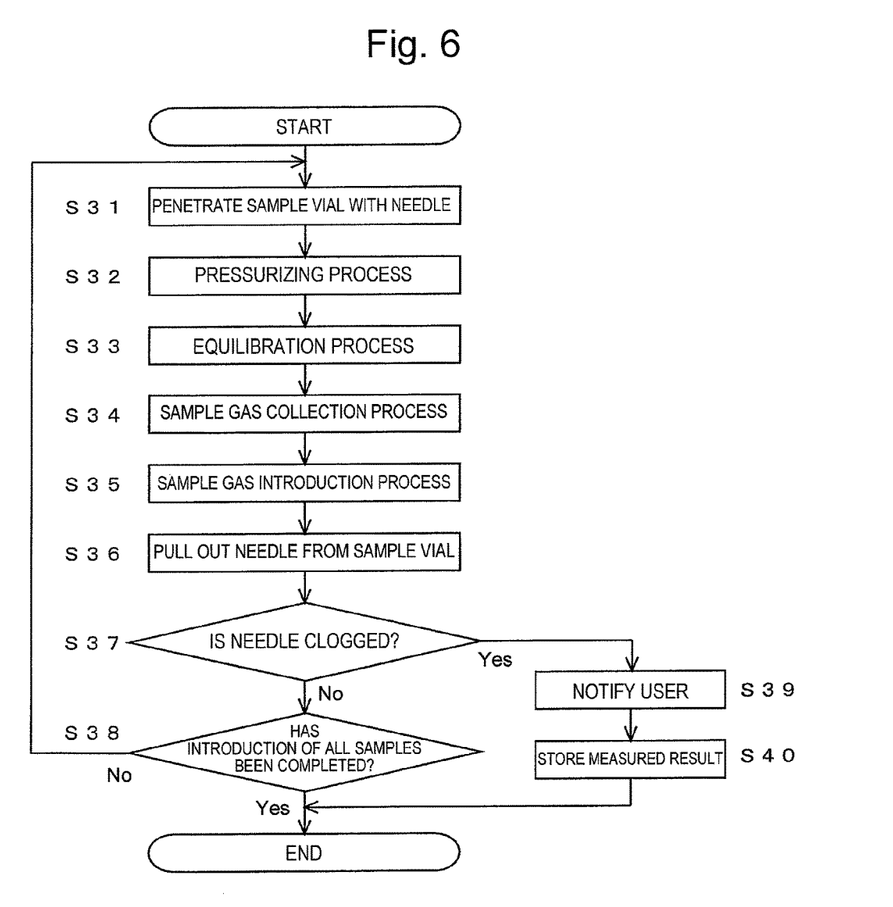
FIG. 6 is a flowchart showing operation of the headspace sampler according to this embodiment.

Subsequently, operations of the headspace sample analyzer according to this embodiment during sample gas introduction into a gas analyzer are described with reference to a flowchart of FIG. 6.

First, the cover 12 of one sample container 11 among multiple sample containers (not shown) set in the sampling unit 100 is pierced with the needle 10, and the distal end of the needle 10 is disposed in the upper space in the sample container 11 (step S31). Subsequently, the foregoing pressurizing process (step S32), the equilibration process (step S33), the sample gas collection process (step S34) and the sample gas introduction process (step S35) are executed. It should be noted that these processes are basic operations for collecting a sample, and the same as those of the device in FIG. 8 having already been described. Accordingly, the detailed description is omitted.

Figure 7:
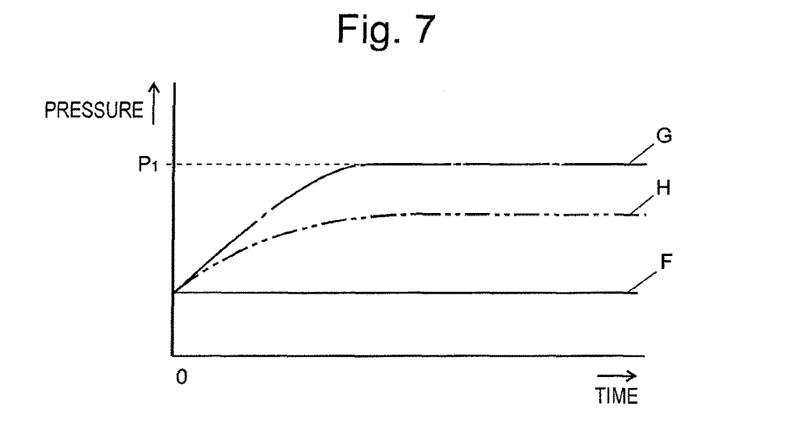
FIG. 7 is a diagram showing an example of a pressure curve in this embodiment.

Subsequently, at the time of completion of the sample gas introduction process (step S35), the channel switching valve 20 is switched to the load state. In the state where the solenoid valves SV1 and SV2 are closed, the needle 10 is pulled out from the sample container 11 (step S36) and the solenoid valve SV1 is opened to introduce the pressure gas into the channel F1. Here, after the moment of opening the solenoid valve SV1, the measured value of the pressure sensor 70 is monitored by the clogging determiner 85 and a pressure curve as shown in FIG. 7 is created. On the other hand, the storage 83 preliminarily stores an ideal pressure curve (i.e., in the case of assumption where there is no clogging in the needle 10) preliminarily calculated based on the piping configuration of the sampling unit 100 and delivery conditions of the pressure gas. At the point in time when a predetermined period of time has elapsed after opening of the solenoid valve SV1, the clogging determiner 85 compares a pressure curve created based on the measured values of the pressure sensor 70 with the ideal pressure curve, and determines whether the needle 10 is clogged or not based on whether the degree of coincidence between both the curves is equal to or higher than a predetermined threshold or not (step S37).

Immediately after the solenoid valve SV1 is opened in the foregoing step S37, the measured value of the pressure gage provided in the pressure control device 61 becomes lower than the target value $P_1$. Then, the on-off valve in the pressure control device 61 is opened, and the pressure gas flows from the gas inlet 41 into the channel F2. At this time, if there is no clogging in the needle 10, the pressure gas flows from the distal end of the needle 10 to the outside. Accordingly, the pressure in the channels F2 and F1 and a path from the branching pipe T1 to the solenoid valve SV2 on the channel F3 hardly increases. Thus, the measured value of the pressure sensor 70 at this time is indicated, for example, by the line F in FIG. 7. On the contrary, if the needle 10 is clogged, the pressure in the channels F2 and F1 and a path from the branching pipe T1 to the solenoid valve SV2 of the channel F3 increases. Then, the measured value by the pressure sensor 70 is indicated by the line G or the line H in FIG. 7.

When the measured value by the pressure sensor 70 reaches the target value $P_1$ as indicated by the line G in FIG. 7, the measured value by the pressure gage in the pressure control device 61 exceeds the target value $P_1$. Accordingly, the on-off valve is closed and flow of the pressure gas from the gas inlet 41 is stopped. On the other hand, while the measured value by the pressure sensor 70 does not reach the target value $P_1$ as indicated by the line F or the line H in FIG. 7, neither does the measured value by the pressure gage in the pressure control device 61 reach the target value $P_1$, and the on-off valve is not closed. Thus, the pressure gas continues to flow from the gas inlet 41 into the channel F2 until the solenoid valve SV1 is closed.

If the pressure curve created based on the measured value of the pressure sensor 70 substantially matches with the ideal pressure curve (line F in FIG. 7), the clogging determiner 85 of this embodiment determines that the needle 10 is not clogged. If the curve is largely different from the ideal pressure curve F as indicated by the line G or the line H in FIG. 7, this determiner determines that the needle 10 is clogged. It should be noted that, instead of creation of the pressure curve as described above, whether there is clogging of the needle 10 or not may be determined by comparing the measured value of the pressure sensor 70 at a predetermined point in time after the solenoid valve SV1 is opened with a value preliminarily calculated as an ideal pressure value at this point in time.

If it is determined that the needle 10 is clogged in step S37, the notification unit 84 notifies the user of this clogging (step S39), and closes the solenoid valve SV1. The measured value of the pressure sensor 70 obtained during a period immediately after the needle 10 is pulled out from the sample container 11 and the solenoid valve SV1 is opened in the foregoing steps S36 and S37 to completion of the determination and/or the determination result in the foregoing step S37 are stored in the storage 83 (step S40), and the operation of the sampling unit 100 is stopped. It should be noted that recording of the measured value or the determination result into the storage 83 may be performed irrespective of the determination result in the clogging determiner 85.

If it is determined that the needle 10 is not clogged in the foregoing step S37, the solenoid valve SV1 is closed and it is subsequently determined whether introduction of sample gas into the column has been completed for all the sample containers set in the sampling unit 100 or not (step S38). If the introduction for all the samples has been completed, the operation of the sampling unit 100 is finished. On the other hand, if any sample having not been introduced remains, the processing returns to step S31, and the operations of steps S31 to S38 are repeatedly executed until the introduction is completed for all the samples.

As described above by the headspace sampler according to this embodiment, the pressure sensor is provided on the upstream side of the solenoid valve SV2 on the channel F3, which allows the pressure applied to this needle to be measured during introduction of the pressure gas into the channel F2 in the state of closing the solenoid valve SV2. Accordingly, it can be easily detected whether the needle 10 is clogged or not.

Furthermore, the above example adopts the configuration of notifying the user of clogging of the needle 10 and subsequently stopping the operation of the sampling unit 100 automatically. Alternatively, the user may be allowed to select whether to stop or continue the operation of the sampling unit 100 when the notification is issued. Alternatively, the user may preliminarily set whether the operation of the sampling unit 100 is stopped or continued when it is determined that the needle 10 is clogged, and the determination may be stored in the storage 83, and then the sampling unit 100 may be controlled according to the setting. It should be noted that even if the user selects the continuation of the operation of the sampling unit 100, the measurement value of the pressure sensor 70 and/or the determination results of the clogging determiner 85 are recorded in the storage 83. Accordingly, the record may be referred to after the process, and only a sample on which clogging of the needle occurs may be analyzed again. If the analysis result by the gas analyzer is inappropriate, the cause can be identified by referring to the record after the process.

It should be noted that the above example adopts the configuration of determining clogging of the needle each time when the introduction of the sample gas into the gas analyzer is completed for one sample container. However, timing of determination is not limited to that in the above description. For example, clogging determination as described above may also be performed before the first sample container is penetrated with the needle. Accordingly, it can be prevented that the sample container is penetrated with the needle without awareness that the needle is clogged to thus waste the valuable sample. Alternatively, a configuration may be adopted that performs determination every time when introduction of the sample gas into the column is completed for a predetermined number of sample containers, or a configuration may be adopted that determination may be performed at appropriate timing pursuant to designation by the user.

Furthermore, in the above embodiment, the pressure sensor 70 is provided between the branching pipe T1 and the solenoid valve SV2. Alternatively, also in the case of providing the pressure sensor 70 at one of positions comprised of a position between the solenoid valve SV1 and the branching pipe T1, a position between the branching pipe T1 and the port b of the channel switching valve 20, a position between the pressure control device 61 and the solenoid valve SV1 and a position on the channel F1, the same effects as described above can be achieved. A configuration may be adopted where clogging of the needle may be determined based on the measured value of the pressure gage provided in the pressure control device 61 (in this case, the pressure gage corresponds to the pressure sensor in the present invention).

Thus, modes for implementing the present invention have been described using the embodiments. However, the present invention is not limited to the foregoing embodiments. An appropriate change is allowed within the scope of the spirit of the present invention. For example, in the foregoing embodiments, the configuration performs any one of determination of a leak of gas in the sample container and determination of clogging of the needle. Alternatively, a configuration may be adopted that performs both determinations in one device. In this case, the control unit 200 is provided with both the leak determiner 82 and the clogging determiner 85.

REFERENCE SINGS LIST

100 . . . Sampling Unit
200 . . . Control Unit
10 . . . Needle
11 . . . Sample Container
12 . . . Cover
20 . . . Channel Switching Valve
30 . . . Measuring Pipe
41, 42 . . . Gas Inlet
51, 52 . . . Gas Outlet
61 . . . Pressure Control Device
62 . . . Flow Rate Control Device
70 . . . Pressure Sensor
81 . . . Operation Controller
82 . . . Leak Determiner
83 . . . Storage
84 . . . Notification Unit
85 . . . Clogging Determiner

The invention claimed is:
1. A headspace sampler, comprising:
a sample gas collection channel whose one end communicates with a needle;
a pressure gas introduction channel and an exhaust channel that communicate with another end of the sample gas collection channel in parallel via a branching pipe;
a first on-off valve provided in the pressure gas introduction channel;
a second on-off valve provided in the exhaust channel;
a pressure sensor provided at one of positions comprised of a position on the sample gas collection channel, a position on the pressure gas introduction channel, and a position between the branching pipe and the second on-off valve of the exhaust channel, and for measuring a pressure in the channel at the position;
gas leak determiner comprising a processor configured to execute processor-executable instructions
for penetrating a sample container with the needle, and subsequently introducing a pressure gas into the sample container through the pressure gas introduction channel by opening the first on-off valve while the second on-off valve is closed, and
for determining a leak of gas from the sample container based on a measurement result of the pressure sensor during the pressure gas introduction into the sample container wherein the first on-off valve is opened and the second on-off valve is closed; and
storage means for storing a target pressure value which is an ideal measured value of the pressure sensor at a predetermined time after the start of an introduction of the pressure gas into the sample container by the gas leak determiner, wherein:

the gas leak determiner determines that there is a leak of gas from the sample container in any of the following cases:

when a measured value of the pressure sensor at the predetermined time after the start of the introduction of the pressure gas is lower than the target pressure value; or when the time at which the measured value of the pressure sensor reaches the target pressure value after the start of the pressure gas introduction is later than the predetermined time.

2. The headspace sampler according to claim 1, further comprising storing means for storing a determination result by processor of the gas leak determiner.

3. The headspace sampler according to claim 1, further comprising notification means for notifying a user of occurrence of a leak of gas when the processor of the gas leak determiner determines the occurrence of the gas leak.

4. The headspace sampler according to claim 1, further comprising:

clogging determiner comprising a processor configured to execute processor-executable instructions for delivering the pressure gas into the pressure gas introduction channel by closing the second on-off valve and opening the first on-off valve, and for determining clogging of the needle based on a measured result of the pressure sensor.

5. The headspace sampler according to claim 4, further comprising storing means for storing a determination result by the processor of the clogging determiner.

6. The headspace sampler according to claim 4, further comprising notification means for notifying a user of occurrence of clogging when the processor of the clogging determiner determines the occurrence of clogging.

7. The headspace sampler according to claim 1, wherein the pressure sensor is provided between the branching pipe and the second on-off valve of the exhaust channel.

8. The headspace sampler according to claim 1, further comprising a channel switching valve provided between the sample gas collection channel and the branching pipe, and for switching a connection state therebetween.

9. The headspace sampler according to claim 8, further comprising a measuring pipe having a prescribed volume and connected to the channel switching valve, wherein:

the channel switching valve changes a state where the measuring pipe is inserted between the sample gas collection channel and the branching pipe and a state where the sample gas collection channel and the branching pipe are shorted away from each other.

* * * * *